United States Patent [19]
Ambrosini

[11] 3,948,249
[45] Apr. 6, 1976

[54] METHOD AND APPARATUS FOR DETECTING AND IDENTIFYING A COW IN HEAT

[76] Inventor: Herman J. Ambrosini, 4265 Hall Road, Santa Rosa, Calif. 95401

[22] Filed: Mar. 31, 1975

[21] Appl. No.: 563,696

[52] U.S. Cl. .................................. 128/2 H; 119/1
[51] Int. Cl.² .......................................... A61B 5/00
[58] Field of Search ............ 128/2 A, 2 H, 2 R, 2 S; 119/1, 15.6, 20, 51 R, 54, 75, 159; 73/349; 40/300; 340/227 R, 228

[56] References Cited
UNITED STATES PATENTS

| | | | |
|---|---|---|---|
| 3,531,642 | 9/1970 | Barnes et al. ........................ | 128/2 H |
| 3,781,837 | 12/1973 | Anderson et al. ................... | 128/2 H |
| 3,788,276 | 1/1974 | Propst et al. ....................... | 119/51 R |
| 3,824,989 | 7/1974 | Horner et al. ....................... | 128/2 H |
| 3,844,273 | 10/1974 | Polson ................................. | 128/2 R |

*Primary Examiner*—William E. Kamm
*Attorney, Agent, or Firm*—Melvin R. Stidham

[57] ABSTRACT

Method and apparatus for detecting and marking cow's in heat utilizing a heat sensitive current generator to scan the cow's backs and generate a current in response to detection of a zone at elevated temperature, characteristic of the tail head of a cow irritated by repeated mounting by other cows. A solenoid valve opens by the current so generated to porject a marking dye onto the cow's back.

5 Claims, 4 Drawing Figures

METHOD AND APPARATUS FOR DETECTING AND IDENTIFYING A COW IN HEAT

BACKGROUND OF THE INVENTION

Dairy cattle, which are maintained under close supervision and in a relatively confined area are generally bred by artificial insemination. Inasmuch as the time during which a cow is in heat is relatively short, it is of considerable importance to be able to detect a cow in heat as early as possible and to be able to single her out and separate her for artificial insemination. It is recognized that a cow in heat will permit other cows to mount her, generally during the early stages of a heat. Various detecting devices have been provided which indicate that a cow has been mounted, but such devices may be triggered by a single mounting and are not reliable indicators that a cow is actually in heat. I have determined that when a cow is in heat and submits to repeated mountings from the rest of the cows, there is caused an extreme irritation on her tail head which produces a localized zone there, warmer then the rest of the body.

OBJECTS OF THE INVENTION

It is an object of this invention to provide a method and apparatus for detecting a cow in heat.

It is a further object of this invention to provide a method and apparatus for detecting a warm zone adjacent a cow's tail.

It is a further object of this invention to provide an apparatus which will detect and mark a cow in heat and issue a positive signal that a cow has been so detected.

Other objects and advantages of this invention will become apparent from the description to follow when read in conjunction with the accompanying drawings.

BRIEF SUMMARY OF THE INVENTION

In carrying out this invention, I provide an infrared temperature detector which scans each cow's back as she passes beneath. The presence of a localized warm zone on the cow's back will generate an electric signal which sounds an audible alarm and energizes a solenoid which opens a valve to allow a stream of marking liquid to be projected through a nozzle onto the cow's back.

DESCRIPTION OF A PREFERRED EMBODIMENT

Figure 4:
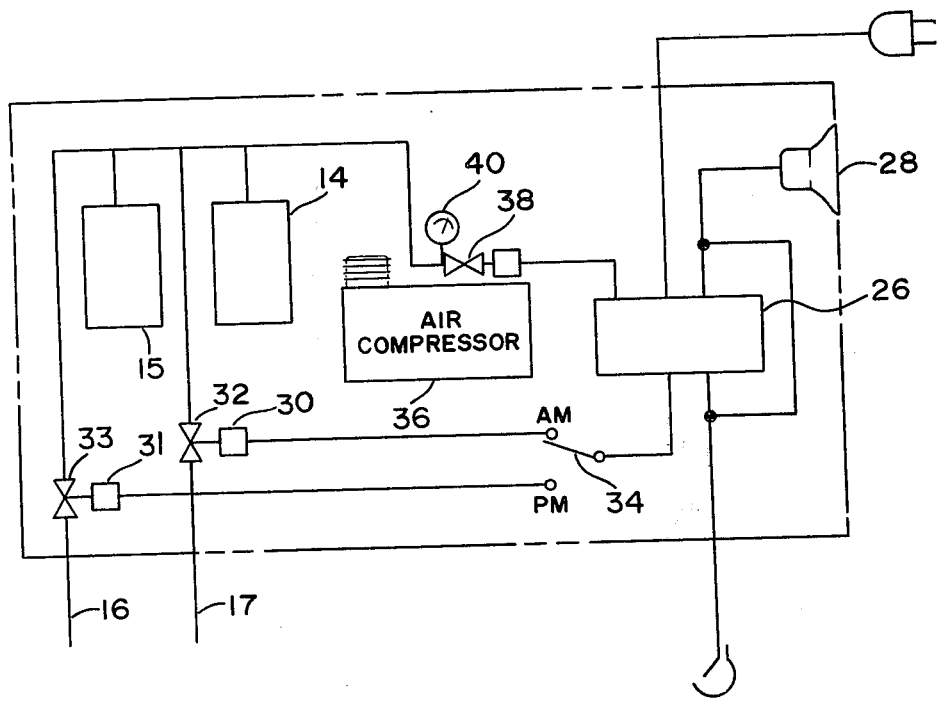
FIG. 4 is a schematic wiring diagram incorporated into the detecting and marking device.
Figure 1:
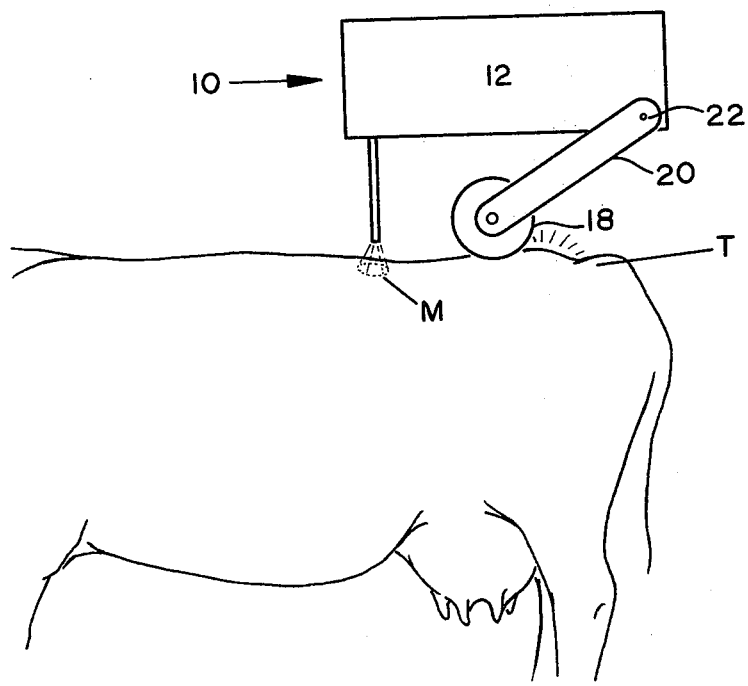
FIG. 1 is an elevation view of a detecting and marking device of this invention.
Figure 3:
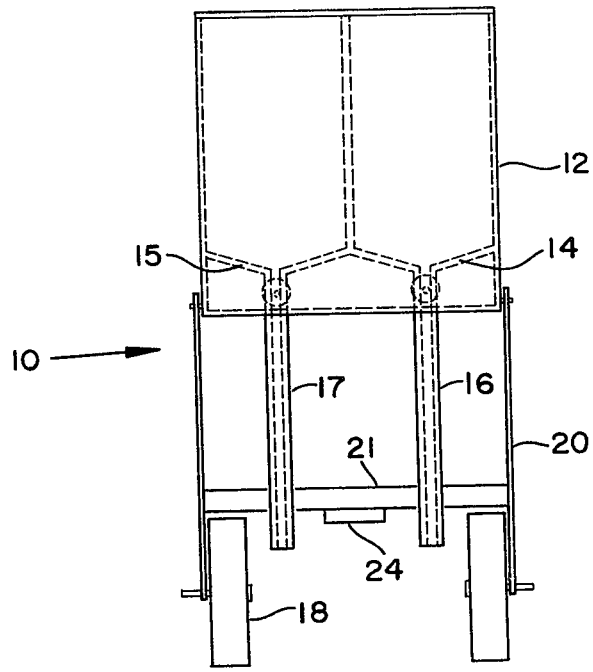
FIG. 3 is an end view of the device.
Figure 2:
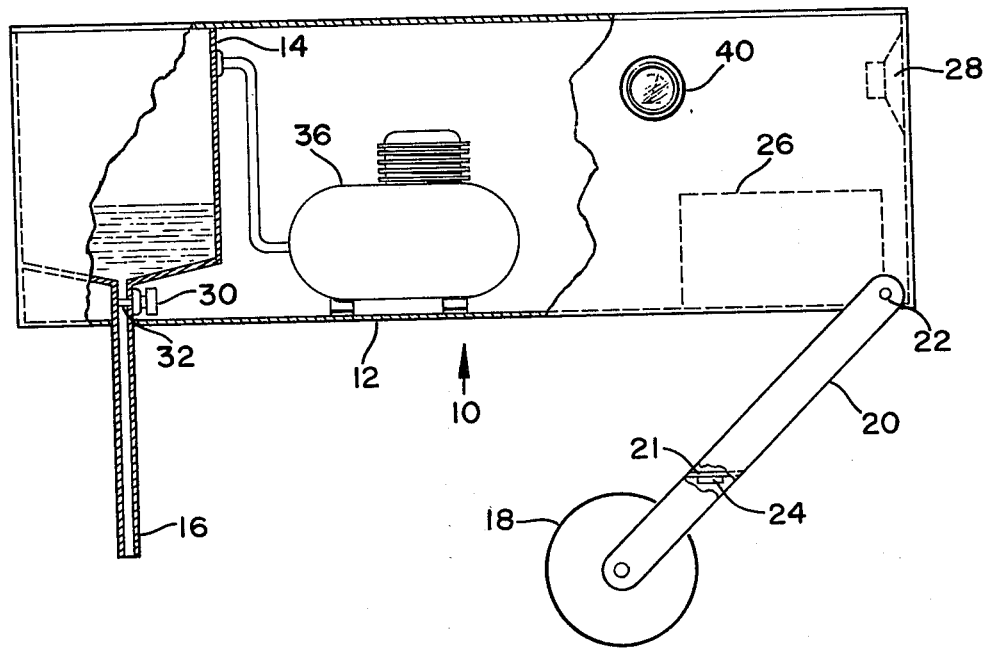
FIG. 2 is an enlarged elevation view, partially in section of the identifying and marking device.

Referring now to FIGS. 1 to 3 with greater particularity, the detecting and marking device 10 of this invention includes a frame or housing 12 in which are contained one or more dye or paint receptacles 14 and 15. Depending from each receptacle is a conduit or nozzle 16, 17 which is adapted to project a marking M (FIG. 1) of a selected color onto the back of a cow who is detected to be in heat. This temporarily brands the cow and marks her for separation from the herd for the purpose of breeding her. The selection and identifying procedure may be carried out by placing the detecting and marking device 10 in any suitable passageway or gateway (not shown) through which the cows are regularly directed to and from pasture or to and from the milking barn. The particular passageway selected must be suitably restricting so that the cows are obliged to pass under the housing 12 and, as shown, under a pair of rollers 18 which are rotatably carried on the ends of arms 20 pivotably mounted on the housing 12.

Carried on the arms 20, as on a cross-member 21 is an infra-red temperature detector, 24 whereby as the rollers 18 roll along each cow's back, the temperature detector will be carried at a fairly uniform distance above the cow's back despite variations from one animal to the next. When a zone of elevated temperature, as for example tail head T, which has been irritated by the repeated mounting of other cows, a current is transmitted from the infra-red detector 24 to suitable electronic signal amplifier 26, which strengthens the signal to a usable level. Then, the signal so amplified activates a suitable audio alarm, as for example, a bell or a horn 28, to alert the dairyman that a cow in heat has been detected. At the same time, the appropriate one of two solenoids 30 and 31, dependent upon the position of a switch 34 is energized to open a valve 32,33 controlled thereby to clear the nozzle 16 or 17 momentarily to allow a quantity of paint or dye to be projected onto the cow's back. The resultant mark M provides ready means of identifying and selecting the cow for removal from the herd.

The paint in the two containers 14 and 15 are preferably of different colors whereby the cow may be marked to show the time of day at which her condition was detected. For example, the switch 34 may be set to condition only the solenoid 30 in the morning, as the cows come into the milking barn or leave for pasture, and to condition the solenoid 31 in the evening when the cows return. That is, only the paint in container 14 will be applied in the morning and the paint in container 15 will be applied in the evening. Hence, the color of paint on the cow's back will readily indicate the time of day at which her condition was detected. The paint containers 14 and 15 are maintained under pressure by means of an air compressor 36 from which the air passes through a suitable reducing valve 38 set to maintain a desired pressure level indicated by a pressure gauge 40.

If desired, the pneumatic system, including the air compressor 36, together with the amplifying means 26 could be positioned remotely from the dye containers 14 and 15 and nozzles 16 and 17, whereby a plurality of such containers could be controlled from the remote station.

While this invention has been described in conjunction with a preferred embodiment thereof, it is obvious that changes and modifications therein may be made by those skilled in the art without departing from the spirit and scope of this invention, as defined by the claims appended hereto.

What I claim as invention is:

1. Apparatus for detecting a cow in heat comprising:
    a frame member positioned to allow a cow to pass beneath it;
    a heat sensitive member on said frame member conditioned to generate a current in response to the presence of a zone of a cow's back at elevated temperatures;

a first container for marking fluid mounted on said frame;
a conduit from said container opening below said frame in advance of said heat sensitive member;
an on-off valve in said conduit; and
valve control means connected to said heat sensitive member and operable in response to an electrical signal to open said valve.

2. The apparatus defined by claim 1 including:
an audio signal device electrically connected to said heat sensitive member.

3. The apparatus defined by claim 1 including:
means for maintaining a gas pressure in said container.

4. The apparatus defined by claim 1 including:
a second container for marking fluid on said frame adjacent to said first container;
a second conduit opening from said second container;
a second on-off valve in said second conduit;
a second valve control means to open said valve in response to an electrical signal form said heat sensitive member; and
switch means for selectively connecting said first and second valve control means to said heat sensitive member.

5. A method for detecting a cow in heat comprising:
scanning a cow's back with heat sensitive means to detect the presence of a localized zone at elevated temperature in the area of a cow's tail head; and
applying a mark to the cow upon the detection of said elevated temperature.

* * * * *